(12) United States Patent
Howland

(10) Patent No.: US 12,117,388 B2
(45) Date of Patent: Oct. 15, 2024

(54) METHOD FOR BACTERIAL DETECTION USING FILM FORMATION PROMOTION WITH ENHANCED CORROSION IMBALANCE

(71) Applicant: David Robert Howland, Grass Valley, CA (US)

(72) Inventor: David Robert Howland, Grass Valley, CA (US)

(*) Notice: Subject to any disclaimer, the term of this patent is extended or adjusted under 35 U.S.C. 154(b) by 726 days.

(21) Appl. No.: 16/904,870

(22) Filed: Jun. 18, 2020

(65) Prior Publication Data
US 2021/0003497 A1   Jan. 7, 2021

Related U.S. Application Data

(63) Continuation of application No. 15/656,729, filed on Jul. 21, 2017, now Pat. No. 11,054,362.

(51) Int. Cl.
| | |
|---|---|
| *G01N 17/04* | (2006.01) |
| *C12Q 1/04* | (2006.01) |
| *G01N 1/44* | (2006.01) |
| *G01N 17/00* | (2006.01) |

(52) U.S. Cl.
CPC ............ *G01N 17/04* (2013.01); *C12Q 1/04* (2013.01); *G01N 1/44* (2013.01); *G01N 17/008* (2013.01)

(58) Field of Classification Search
CPC ........ G01N 1/44; G01N 17/008; G01N 17/04; C12Q 1/04
See application file for complete search history.

(56) References Cited

U.S. PATENT DOCUMENTS

2005/0272146 A1* 12/2005 Hodge ................ B01F 35/513
435/289.1

* cited by examiner

*Primary Examiner* — Lydia Edwards
(74) *Attorney, Agent, or Firm* — Michael A. Guth

(57) ABSTRACT

A system and method adapted to have high sensitivity to the formation of biofilm by mixed community bacteria in fluids. The system enhances corrosion imbalance by differentiating conditions between metal sensor elements immersed in the liquid being monitored. The liquid may be diverted to and flowed through a sample chamber where adjacent sensor elements may reside in different flow velocity or temperature regions. The differentiated conditions allow for different film formation on one of the sensor elements relative to the other, and also more quickly than in the main system from which the sampled liquid has been diverted. The differentiated formation allows the use of measurement of polarization current between the metal sensors to produce data with superior resolution relative to prior methods. The speed of film formation promoted by the differentiated conditions allows for determination of risk of film formation in the main system prior to that film's formation in the main system.

10 Claims, 13 Drawing Sheets

METHOD FOR BACTERIAL DETECTION USING FILM FORMATION PROMOTION WITH ENHANCED CORROSION IMBALANCE

CROSS-REFERENCE TO RELATED APPLICATIONS

This application is a continuation of U.S. patent application Ser. No. 15/656,729 to Howland, filed Jul. 21, 2017, which claims priority to U.S. Provisional Application No. 62/483,570 to Howland, filed Apr. 10, 2017, which are hereby incorporated by reference in their entirety.

BACKGROUND

Field of the Invention

This invention relates to the early detection of live water borne biology.

Description of Related Art

In industrial, domestic, and medical aquatic systems there are many factors which can create problems by reducing the efficiency of the process concerned or by creating toxicity problems. For example, water used in most of these systems will usually contain some form of living microorganisms which under the conditions in the systems can multiply and cause a number of problems. Initially the microbes may be suspended in the water. These so-called planktonic microorganisms are relatively easy to kill using conventional biocides. Although they can cause problems, for instance if the microorganisms are pathogenic, in general they do not significantly affect the overall efficiency of the system.

The planktonic microorganisms can however become adherent to internal surfaces in the system when they are known as "sessile". Sessile bacteria can proliferate and some bacteria generate a slime composed mainly of polysaccharide and form a film upon the surface. These films contribute to inefficiencies in the systems for various reasons. For instance, the films will reduce efficiency of conductive heat transfer through the surfaces and, since they are highly elastic, increase fluid frictional resistance at the surface dramatically. Furthermore some types of bacteria produce compounds which may be environmentally hazardous or may lead to corrosion of metal in the surface to which the film is attached. Sulphate reducing bacteria or SRB's in particular can give rise to serious corrosion of metal surfaces.

Bacteria in biofilms are in general found to be difficult to get rid of, partly because chemical biocides must penetrate the slime before they reach the target microorganisms deep within the films. Because of the problems that biofilms can create, a dose of a suitable biocide may be periodically necessary to prevent development of films.

The microbial cells growing in biofilm may be physiologically distinct from planktonic cells of the same organism. When a cell switches from planktonic to a biofilm mode of growth, it may undergo a phenotypic shift in behavior in which large suites of genes are differentially regulated.

What is needed is a system and method for determining whether a fluid system, such as a water delivery system, has reached a threshold level of planktonic bacteria of a type or types which will form a biofilm. What is also needed is a system which can determine whether such microbes are present in advance of the formation of a biofilm which interferes with system function.

SUMMARY

Figure 1A:
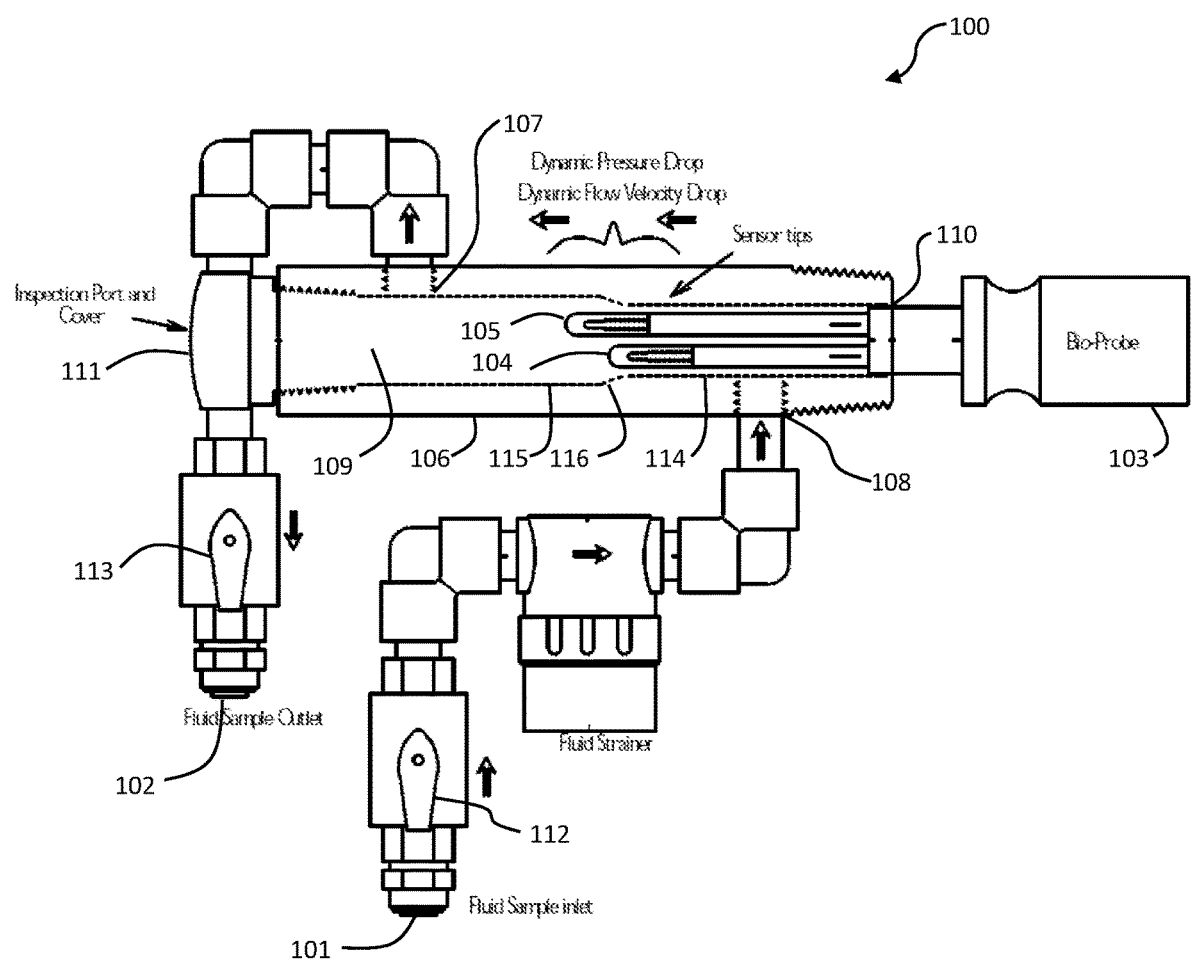
FIG. 1A is a system for bacteria detection using film formation promotion according to some embodiments of the present invention.

A system and method adapted to have high sensitivity to the formation of biofilm by mixed community bacteria in fluids. The system enhances corrosion imbalance by differentiating conditions between metal sensor elements immersed in the liquid being monitored. The liquid may be diverted to and flowed through a sample chamber where adjacent sensor elements may reside in different flow velocity or temperature regions. The differentiated conditions allow for differential film formation on one of the sensor elements relative to the other, and also more quickly than in the main system from which the sampled liquid has been diverted. The differentiated formation allows the use of measurement of polarization current between the metal sensors to produce data with superior resolution relative to prior methods. The speed of film formation promoted by the differentiated conditions allows for determination of risk of film formation in the main system prior to that film's formation in the main system.

DETAILED DESCRIPTION

Groups of otherwise unrelated organisms, which may all be bacteria, may interact by a mechanism of nutrient succession that ensures both cooperation between species and maximum utilization of the primary nutrients. Such groups inevitably have a structural component and they exist as aggregates in the form of flocculents or biofilms. Diffusional resistance to oxygen penetration, coupled with its uptake by aerobic species, can result in the creation of anoxic and reduced microenvironments within the central regions of the consortium of species. A general model for a microbial consortium would therefore be a nutritionally linked group of aerobic, facultative, and anaerobic bacterial species displaying heterotrophic hydrolytic and fermentative activity, acetogenesis, and a terminal oxidative stage involving either methanogenesis or sulphate reduction. In a biofilm, particular organisms exist within appropriate microenvironments which are created by their own and other organisms' activities and are maintained by virtue of the polymeric matrix within which they are imbedded.

Biofilms are dynamic structures. The pattern of their development can be divided into phases of transport of molecules and cells to the substrate, attachment, increase in biomass (cells and extracellular polymeric substances), and detachment. In a multispecies biofilm this situation may be complicated by the requirement for organism A to establish the necessary conditions, for example anaerobiosis, before organism B can become established within the biofilm.

As the understanding of the nature of biological corrosion mechanisms has increased, the terms "biocorrosion" and "microbial corrosion" have been replaced by the term "microbially influenced corrosion". This is a reflection of there being a range of quite different microbial processes involved, and the fact that they operate primarily by stimulating pre-existing electrochemical mechanisms of corrosion rather than by introducing any novel reaction schemes of their own.

The main instances of microbially influenced corrosion resulting from the action of sulphate reducing bacteria are noted with cast iron and mild steel. In the case of buried cast iron pipes, the effect can be dramatic, with the complete removal of the iron leaving behind an apparently unaltered structure which is composed solely of graphite and retains none of the strength of the original material. It is with mild steels, however, that the sulphate reducing bacteria have their major impact.

With the dramatic and damaging impacts the formation of biofilms can have on an operating system it is of vital importance that live bacteria of types which may form a biofilm together be detected prior to the formation of biofilm in the operating system. In embodiments of the present invention, the presence of live film forming planktonic bacteria is detected using a system which promotes microbially influenced corrosion and also film formation in a test chamber at an accelerated rate. This accelerated film formation accentuates differential film growth on sensor tips such that film growth can be detected very quickly. The detection of this differential film growth alerts the system operator that live film forming bacteria are present in fluid of the main operating system, and may raise an alert prior to film having formed in the main operating system. The system operator may then use biocide or other means to prevent film formation in the main operating system.

In some embodiments of the present invention, as seen in FIG. 1A, a system for bacteria detection using film formation promotion is comprised of a test device 100 coupled to and adapted to route fluid from a fluid system, such as a water system, via an inlet tube 101. The inlet tube 101 routes fluid into the chamber inlet 108 of a sample flow chamber 106. In some aspects, fluid from the fluid system is supplied to the inlet tube 101 using a pump which pumps water from the main fluid system. In some aspects, fluid from the fluid system is supplied to the inlet tube 101 via gravity. In some aspects, fluid from the fluid system is metered using a metering pump. In some aspects, the test device 100 is inverted to utilize gravity to create flow in the sample flow chamber 106. In some aspects, a supply pump which pumps water from the main fluid system into the inlet tube 101 is utilized to create flow in the sample flow chamber 106.

In some embodiments, a probe apparatus 103 is removably inserted into an opening 110 in the sample flow chamber 106. The probe apparatus 103 may have a first test probe 104 and a second test probe 105 coupled to a mounting unit adapted to inserted into the opening in the sample flow chamber 106. In some embodiments, as seen in FIG. 1A, the tip of the first test probe 104 and the second test probe 105 are located in different regions within the fluid space 109 of the sample flow chamber 106. The fluid space 109 within the chamber 106 may be of a first, smaller, cross-sectional area in a first region 114 of the fluid space 109, and of a second, larger, cross-sectional area in a second region 115 of the fluid space 109. An enlarging zone 116 may bridge the first region 114 and the second region 115. The tip of the first test probe 104 may be substantially or fully in the first region 114 of the fluid space 109, and the tip of the second test probe 105 may be substantially or fully in the second region 115 of the fluid space 109. In such a configuration, the flow rate around the tip of the first test probe 104 will be different than the flow rate around the tip of the second test probe 105. In such a configuration, the flow rate around the tip of the first test probe 104 will be lower than the flow rate around the tip of the second test probe 105. The differences between the flow rates of the fluid around the tips of the two probes presents a different environment for microbially influenced corrosion and for the formation of biofilm.

The test device 100 may have an inlet valve 112 adapted to shut off or allow fluid flow through the inlet tube 101. The outlet tube 102 may similarly have an outlet valve 113 to shut off or allow fluid flow through the outlet tube. An inspection cover 111 may allow for physical inspection within the system, and the sample flow chamber 106.

Figure 1B:
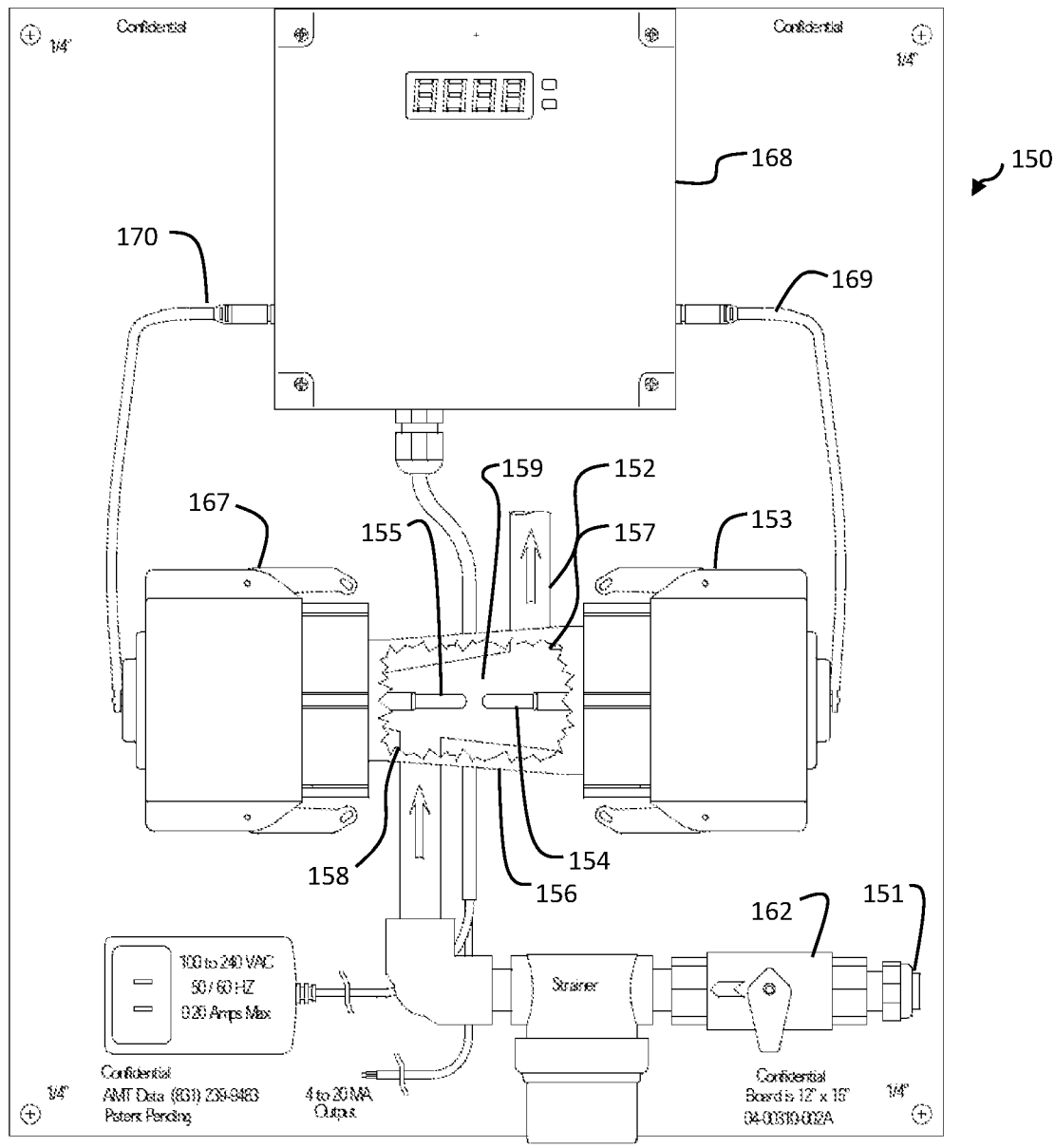
FIG. 1B is a system for bacteria detection using film formation promotion according to some embodiments of the present invention.

In some embodiments of the present invention, as seen in FIG. 1B, a system for bacteria detection using film formation promotion is comprised of a test device 150 coupled to and adapted to route fluid from a fluid system, such as a water system, via an inlet tube 151. The inlet tube 151 routes fluid into the chamber inlet 158 of a sample flow chamber 156. In some aspects, fluid from the fluid system is supplied to the inlet tube 151 using a pump which pumps water from the main fluid system. In some aspects, fluid from the fluid system is supplied to the inlet tube 151 via gravity. In some aspects, the test device 150 is inverted to utilize gravity to create flow in the sample flow chamber 156. In some aspects, a supply pump which pumps water from the main fluid system into the inlet tube 151 is utilized to create flow in the sample flow chamber 156.

In some embodiments, a first probe apparatus 153 is removably inserted into a first opening in the sample flow chamber 156. The probe apparatus 153 may have a first test probe 154 coupled to a mounting unit adapted to be inserted into the first opening in the sample flow chamber 156. A second probe apparatus 167 is removably inserted into a second opening in the sample flow chamber 156. The second probe apparatus 167 may have a second test probe 155 coupled to a mounting unit adapted to be inserted into the second opening in the sample flow chamber 156. In some embodiments, as seen in FIG. 1B, the tip of the first test probe 154 and the second test probe 155 are located in different regions within the fluid space 159 of the sample flow chamber 156. The fluid space 159 within the chamber 156 may be of a first, smaller, cross-sectional area in a first region near the fluid inlet 158 of the fluid space 109, and of a second, larger, cross-sectional area in a second region near the outlet 157 of the fluid space 109. In such a configuration, the flow rate around the tip of the first test probe 104 will be different than the flow rate around the tip of the second test probe 105. In such a configuration, the flow rate around the tip of the first test probe 154 will be lower than the flow rate around the tip of the second test probe 155. The differences between the flow rates of the fluid around the tips of the two probes presents a different environment for the formation of biofilm.

The test device 150 may have an inlet valve 162 adapted to shut off or allow fluid flow through the inlet tube 151. The outlet tube 152 may similarly have an outlet valve 163 to shut off or allow fluid flow through the outlet tube.

The first probe apparatus 153 may be coupled to an electronics unit 168 with a cable 169. The second probe apparatus 167 may be coupled to the electronics unit 168 with a cable 170. The electronics unit may be adapted to provide voltage differential to the two test probes while measuring current flow. The electronics unit may be adapted to provide different voltage differentials, including reversing polarity of the probes. The electronics unit may be adapted to implement instructions which direct the electronics to apply different voltage regimes over time to the probes. The electronics unit may make intermittent or continuous measurement of current flow or other parameters.

Figure 2:
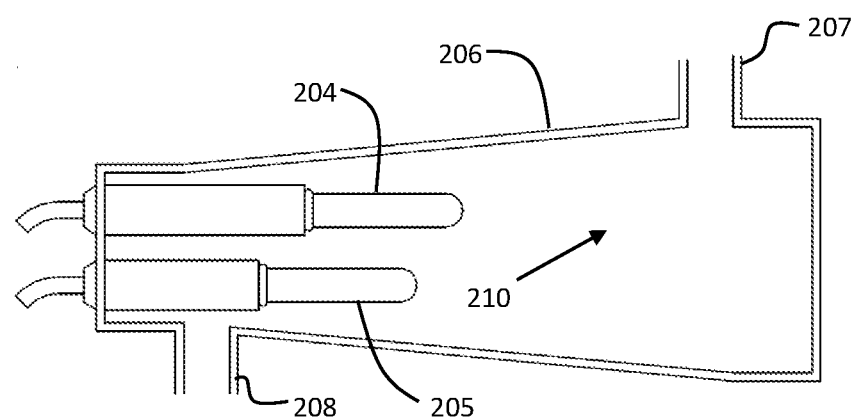
FIG. 2 is a view of a sample flow chamber according to some embodiments of the present invention.
Figure 4:
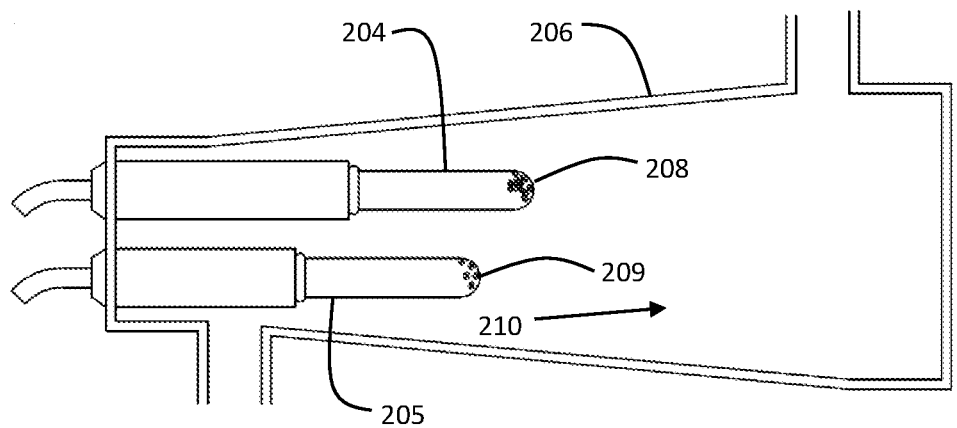
FIG. 4 is a view of a sample flow chamber with some film formation according to some embodiments of the present invention.

In some embodiments of the present invention, as seen in FIG. 2, a sample flow chamber 206 has an inlet 208 and an outlet 207. The sample flow chamber has an increased cross-sectional flow area along the flow direction 210. The first test probe 205 resides in a portion of the sample flow chamber 206 in a higher speed flow area relative to the second test probe 204. Both the first test probe 205 and the second test probe 204 enter into the sample flow chamber 206 from a same end. The different flow rates seen by the two test probes result in different conditions for the formation of biofilms at the two test probes. As seen in illustrative example in FIG. 4, the film growth 209 on the first test probe 205 is different than the film growth 208 on the second test probe 204. In some cases there may be a different amount of film growth on the two tips. In some cases there may be a different type of film grown on the two test tips. In some cases, there may be similar film types on the two probes but in different quantities. In some cases, the differences between the films may be significant enough that the films on the two tips exchange electrons, or other things, with the film on the other tip.

Figure 3:
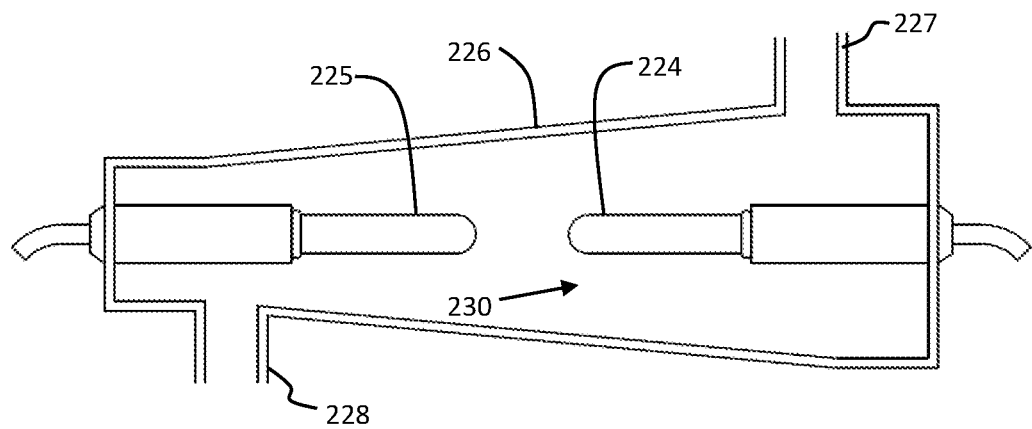
FIG. 3 is a view of a sample flow chamber according to some embodiments of the present invention.
Figure 5:
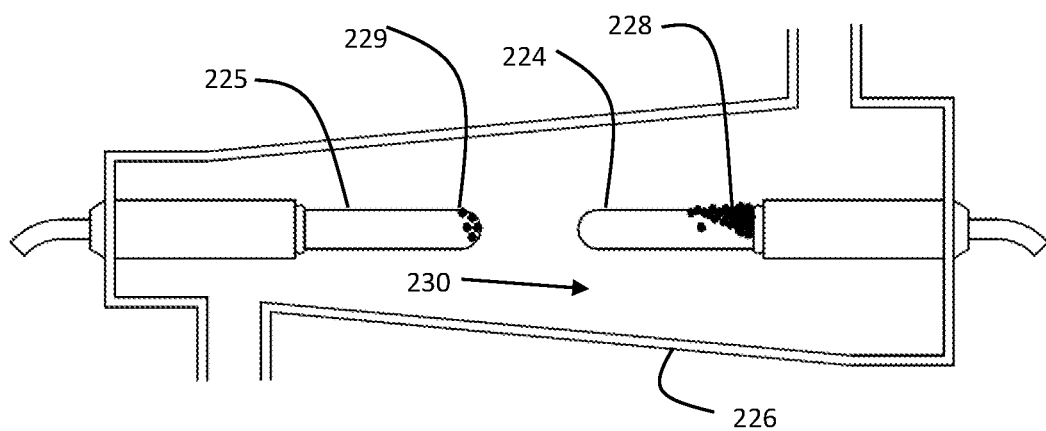
FIG. 5 is a view of a sample flow chamber with some film formation according to some embodiments of the present invention.

In some embodiments of the present invention, as seen in FIG. 3, a sample flow chamber 226 has an inlet 228 and an outlet 227. The sample flow chamber has an increased cross-sectional area along the flow direction 230. The first test probe 225 resides in a portion of the sample flow chamber 226 in a higher speed flow area relative to the second test probe 224. The first test probe 225 enters into the sample flow chamber 226 from a first end, and the second test probe 224 enters into the sample flow chamber 226 from a second end. The different flow rates seen by the two test probes result in different conditions for the formation of biofilms at the two test probes. As seen in illustrative example in FIG. 5, the film growth 229 on the first test probe 225 is different than the film growth 228 on the second test probe 224. In some cases there may be a different amount of film growth on the two tips. In some cases there may be a different type of film grown on the two test tips. In some cases, there may be similar film types on the two probes but in different quantities. In some cases, the differences between the films may be significant enough that the films on the two tips exchange electrons, or other things, with the film on the other tip.

Figure 6:
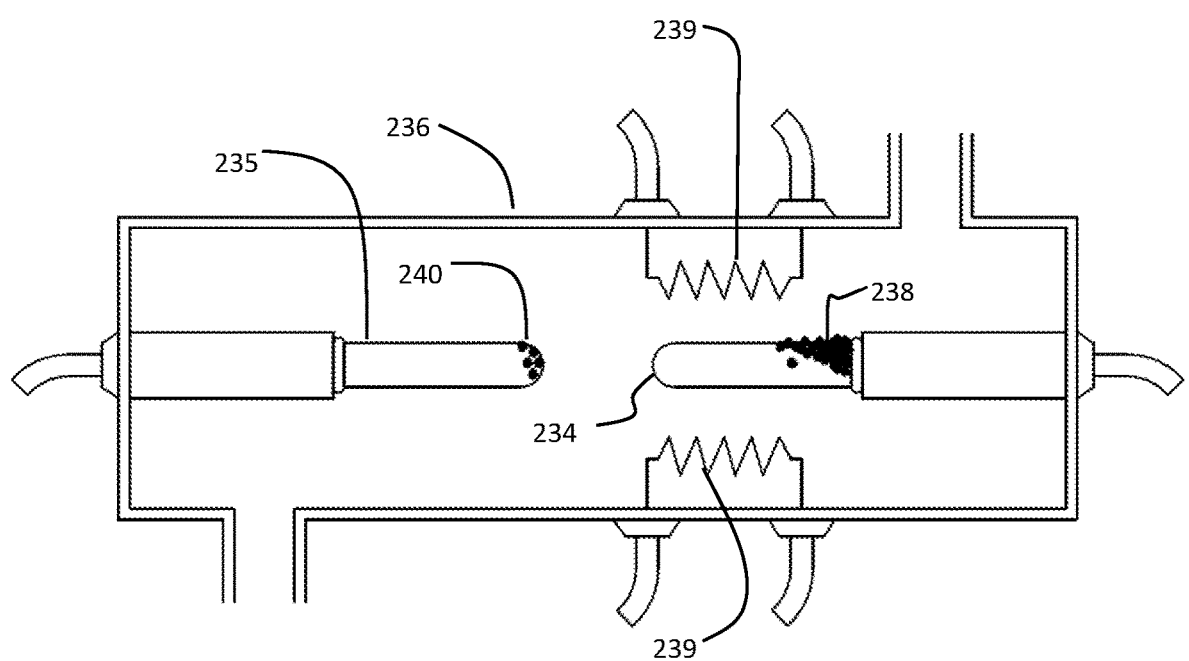
FIG. 6 is a view of a sample flow chamber with some film formation according to some embodiments of the present invention.

In addition to the use of different flow rates to create different growth environments and induce different amounts of microbe influenced corrosion on the test probes, different temperatures may also be used to create different growth environments and induce different amounts of microbe influenced corrosion on the test probes. In some embodiments, as seen FIG. 6, a sample flow chamber 236 has a constant cross-sectional area along the flow direction. A first test probe 235 is seen closer to the inlet into the sample flow chamber and second test probe 234 is seen closer to the outlet from the sample flow chamber. Heaters 239 are used to heat the water near the second test probe 234, and may also heat the second test probe 234. As seen, this creates different growth environments on the two test probes, which then results in an area of microbially influenced corrosion 239 on the first test probe 235 that is different than the area of microbially influenced corrosion 238 on the second test probe 234.

Figure 7:
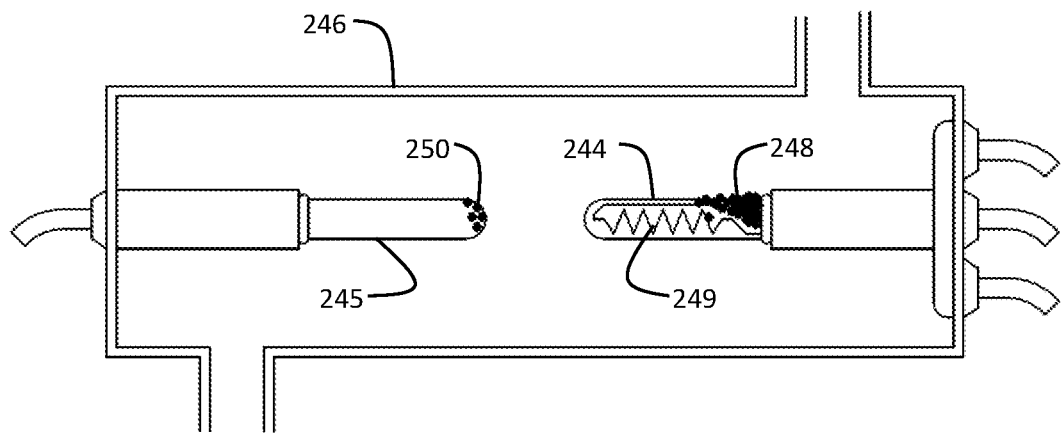
FIG. 7 is a view of is a view of a sample flow chamber with some film formation according to some embodiments of the present invention.

In another embodiment, as seen in FIG. 7, a sample flow chamber 246 has a constant cross-sectional area along the flow direction. A first test probe 245 is seen closer to the inlet into the sample flow chamber and second test probe 244 is seen closer to the outlet from the sample flow chamber. A heater 249 may be embedded within the second test probe 244. As seen, this creates different growth environments on the two test probes, which then results in an area of microbially influenced corrosion 249 on the first test probe 245 that is different than the area of microbially influenced corrosion 248 on the second test probe 244.

In some embodiments, the water temperature at the second probe is 20 C. warmer than at the first probe. In some embodiments, the water temperature is in the range of 10 C. to 60 C. warmer at the second probe.

Figure 9:
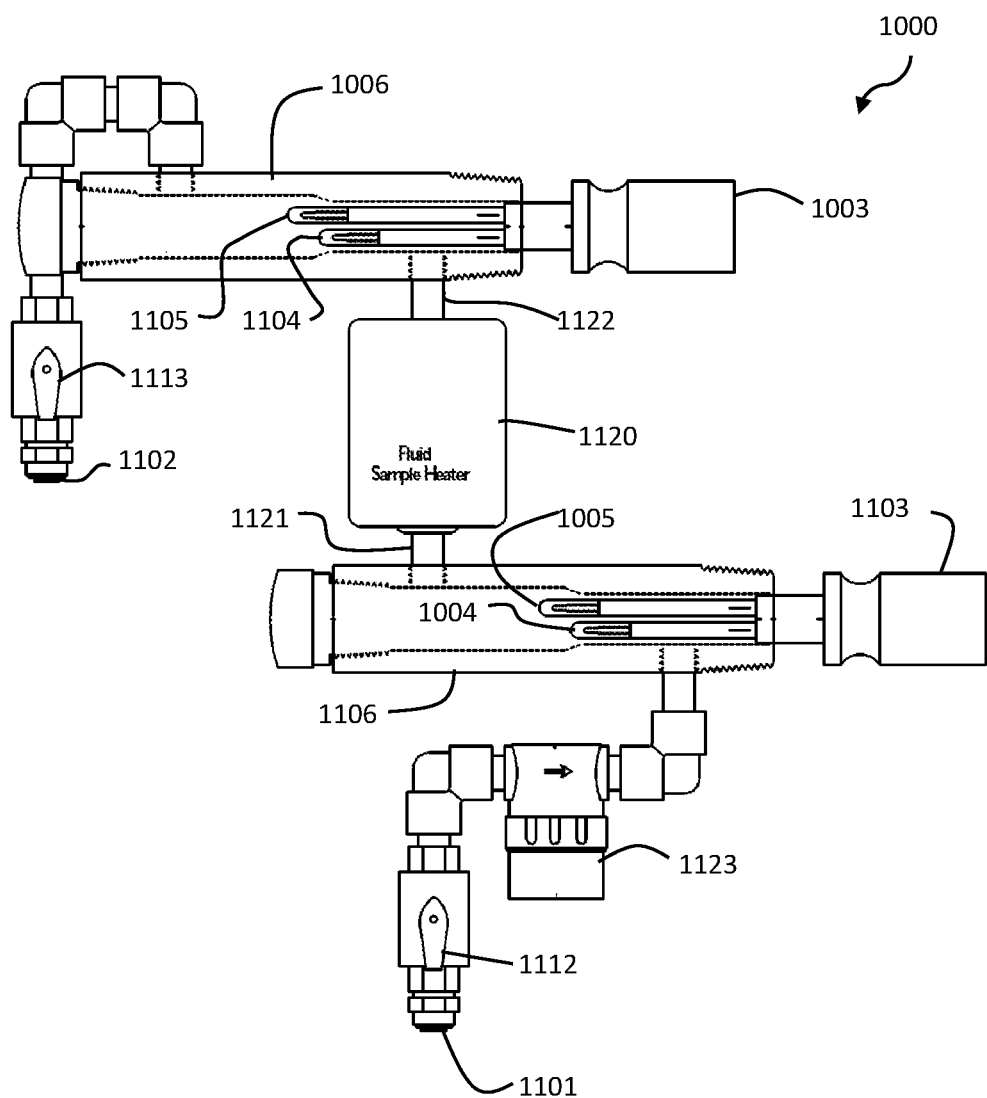
FIG. 9 is a view of a test system with two sample flow chambers according to some embodiments of the present invention.

In some embodiments of the present invention, as seen in FIG. 9, a double chamber system 1000 flows fluid through a first sample flow chamber 1106, then heats the fluid in a fluid heater 1120, and then flows fluid through a second sample flow chamber 1006. Fluid enters the double chamber system 1000 via an inlet 1101 which may be flow controlled by a valve 1112. In some aspects, a strainer 1123 may strain the fluid prior to its delivery into the first sample flow chamber 1106. The first sample test chamber may have a first probe apparatus 1103 which allows for ease in removing and replacing test probes into the first sample flow chamber 1106. The first probe apparatus 1103 may allow for easy insertion of a first test probe 1004 and the second test probe 1005. The sample flow chamber has an increased cross-sectional area along the flow direction. The first test probe 1004 resides in a portion of the sample flow chamber 1106 in a higher speed flow area relative to the second test probe 1005. The different flow rates seen by the two test probes result in different conditions for the formation of biofilms at the two test probes.

The fluid exits the first sample flow chamber 1106 via an outlet 1121. A fluid sample heater 1120 heats the fluid prior to its entry into the second sample flow chamber 1006 via an inlet 1122. The second sample test chamber may have a first probe apparatus 1003 which allows for ease in removing and replacing test probes into the first sample flow chamber 1006. The second probe apparatus 1003 may allow for easy insertion of a first test probe 1104 and the second test probe 1105. The sample flow chamber has an increased cross-sectional area along the flow direction. The first test probe 1104 resides in a portion of the sample flow chamber 1006 in a higher speed flow area relative to the second test probe 1105. The different flow rates seen by the two test probes result in different conditions for the formation of biofilms at the two test probes. In addition, the fluid temperature in the second sample flow chamber 1006 is warmer than in the first sample flow chamber 1106 as a result of having been heated by the fluid sample heater 1120. The environment for microbially enhanced corrosion is thus different in the second sample flow chamber 1006 than in the first sample flow chamber 1106. This second growth environment allows for a second environment for film and corrosion promotion, allowing for an increased likelihood of promoting growth in one of the two sample flow chambers than may be possible with a single growth environment.

Figure 8:
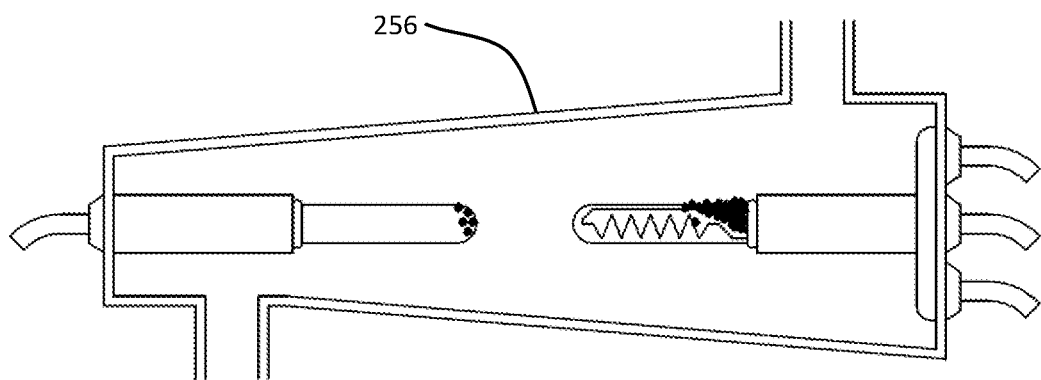
FIG. 8 is a view of is a view of a sample flow chamber with some film formation according to some embodiments of the present invention.

In some embodiments, as seen in FIG. 8, the two test probes not only reside in areas within the sample flow chamber 256 which have different flow rates but the two test probes are also at different temperatures.

Figure 10:
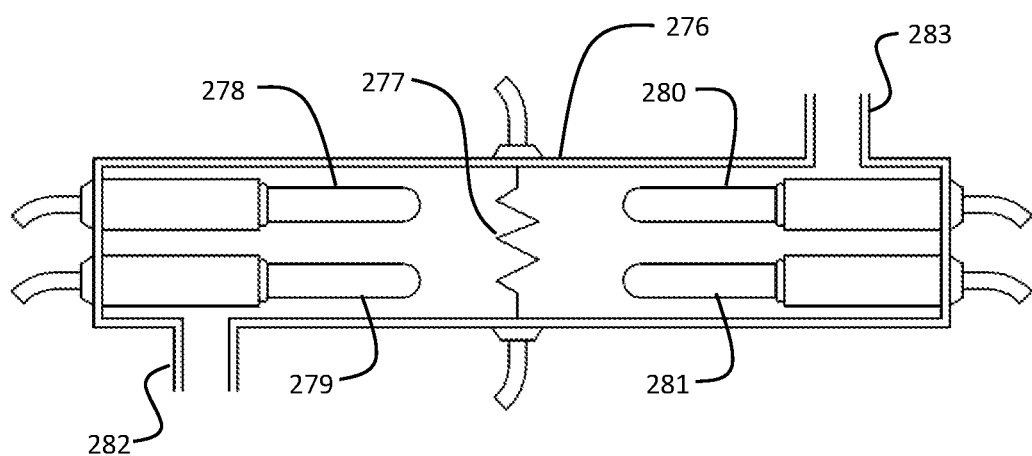
FIG. 10 is view of a sample flow chamber with two sets of test probes according to some embodiments of the present invention.

In some embodiments, as seen if FIGS. 9 and 10, the sample flow chambers each have two sets of test probes. In some embodiments, as seen in FIG. 10, a sample flow chamber 276 with an inlet 282 and an outlet 283 with a heater 277 between the sets of test probes. The first test probes 278, 279 are in a first environment wherein the fluid flow has not yet been heated by the heater 277. The heater 277 heats the fluid so that the fluid flowing by the second test probes 280, 281 is warmer than it was at the first test probes. Where mixed species biology may be present in fluid, their presence may be indicated between two or more sets of sensor pairs where the fluid temperature is higher on one or more sets of sensor pairs in the array of sensor pairs. Where biology is not living and not colonizing the sensors in the array, the effects of the difference in temperature serve as a base line in the fluid being monitored. Where the differences in signals become different from the determined base-line, the presence of live mixed species biology may be indicated.

Figure 11:
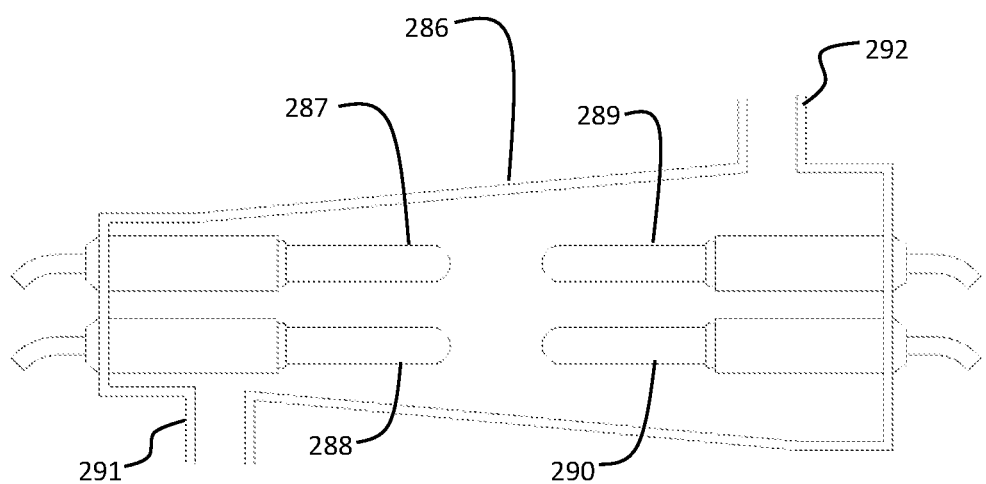
FIG. 11 is view of a sample flow chamber with two sets of test probes according to some embodiments of the present invention.

In some aspects, as seen in FIG. 11, a sample flow chamber 286 with an inlet 291 and an outlet 292 has an increase in cross-sectional flow area between the sets of test probes. The first test probes 287, 288 are in an area where the fluid flow velocity is higher than the fluid flow velocity in the area of the second test probes 289, 290. The first test probes 287, 288 are in a first environment wherein the fluid flow is quicker than further into the chamber. The fluid flow slows down in the area of the second test probes 289, 290.

Figure 12:
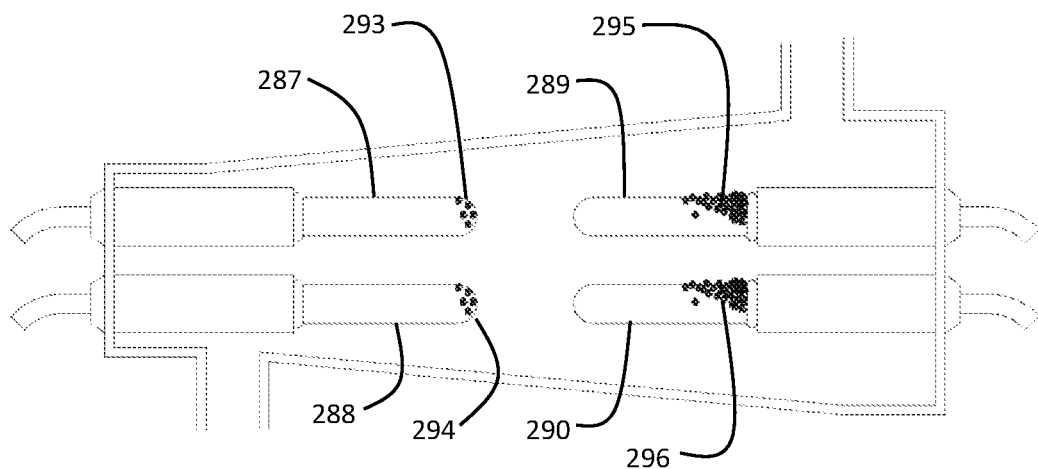
FIG. 12 is view of a sample flow chamber with two sets of test probes and some film formation according to some embodiments of the present invention.

FIG. 12 illustrates the film growth 293, 294 on the first test probes 287, 288 and the film growth 295, 296 on the second test probes 289, 290.

Figure 13:
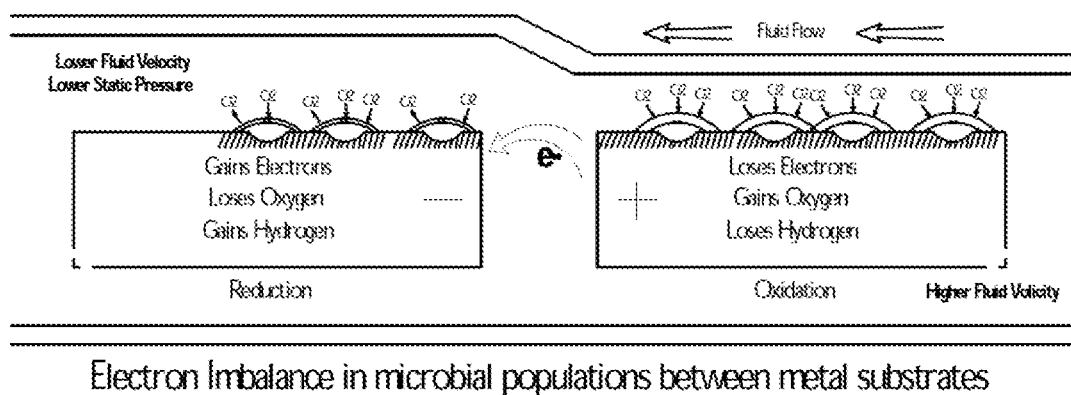
FIG. 13 is an illustrative sketch of microbial populations on metal substrates.

FIG. 13 illustrates an aspect of microbially influenced corrosion seen in systems according to embodiments of the present invention. In a system using test probes, such as test probes made from mild steel, there will be general corrosion even in the absence of any live bacteria. Also, there will be microbially influenced corrosion when there are live bacteria. In a normal situation without differentiated environments, bacteria may begin to influence corrosion without any significant likelihood that bacteria will colonize other than in random patterns. However, by presenting differing environments on the two test probe tips, either by having a different flow rate around each tip, or a different temperature at each tip, or both, it is very likely that the type of colonization will be different. Because of this difference, it is likely that a net electron flow will occur between the bacterially influenced corrosion areas on the two tips. This may occur because there is more oxidation occurring on one tip and more reduction occurring on the other tip. The net electron flow is illustrated in FIG. 13.

In embodiments where there is a fluid pressure difference between the sensors, which will occur in constant flow systems with a difference in flow chamber cross-sectional area, oxygen as a compressible gas may expand when a fluid containing oxygen enters the area with lower pressure. Where two biofilm communities are adjacent to each other, and where one is in an environment where oxygen is forming bubbles as it expands under lower fluid pressure, different biofilm communities will establish and exchange electrons in response to the difference in oxygen concentrations in the fluid.

Figure 14:
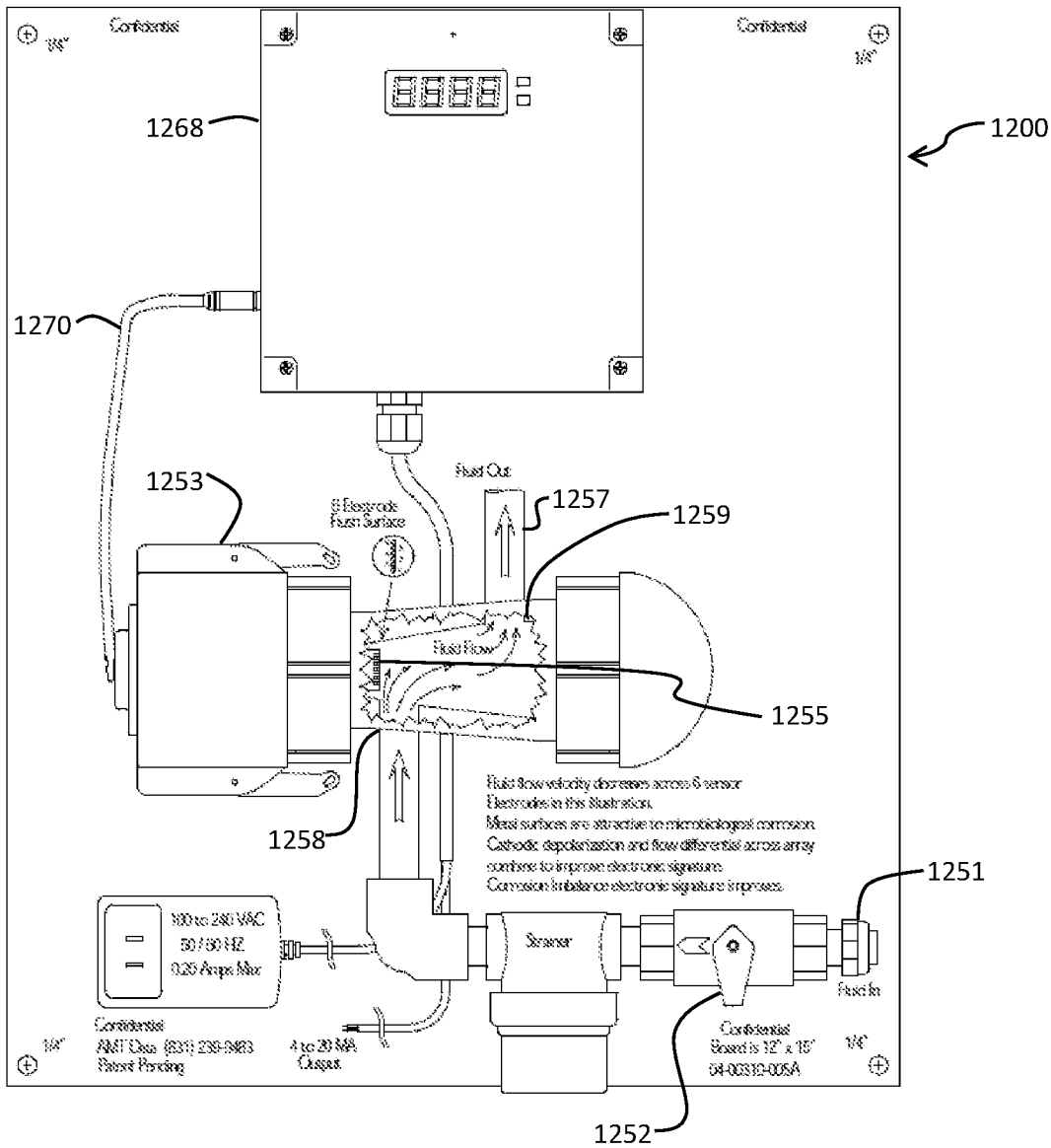
FIG. 14 is a system for bacteria detection using film formation promotion according to some embodiments of the present invention.

In some embodiments, as seen in FIG. 14, a system for bacteria detection using film formation promotion is comprised of a test device 1200 with a sample flow chamber 1259. The sample flow chamber 1259 increases in cross-sectional area along the flow direction between the chamber inlet 1258 and the chamber outlet 1257. Fluid enters through an inlet 1251 which may be controlled with a valve 1252. Fluid exits through an outlet 1257. A test probe apparatus 1253 may be inserted into an opening in the sample flow chamber 1259. An electrical cable 1270 connects the test probe apparatus 1253 to a system electronics 1268.

Figure 15:
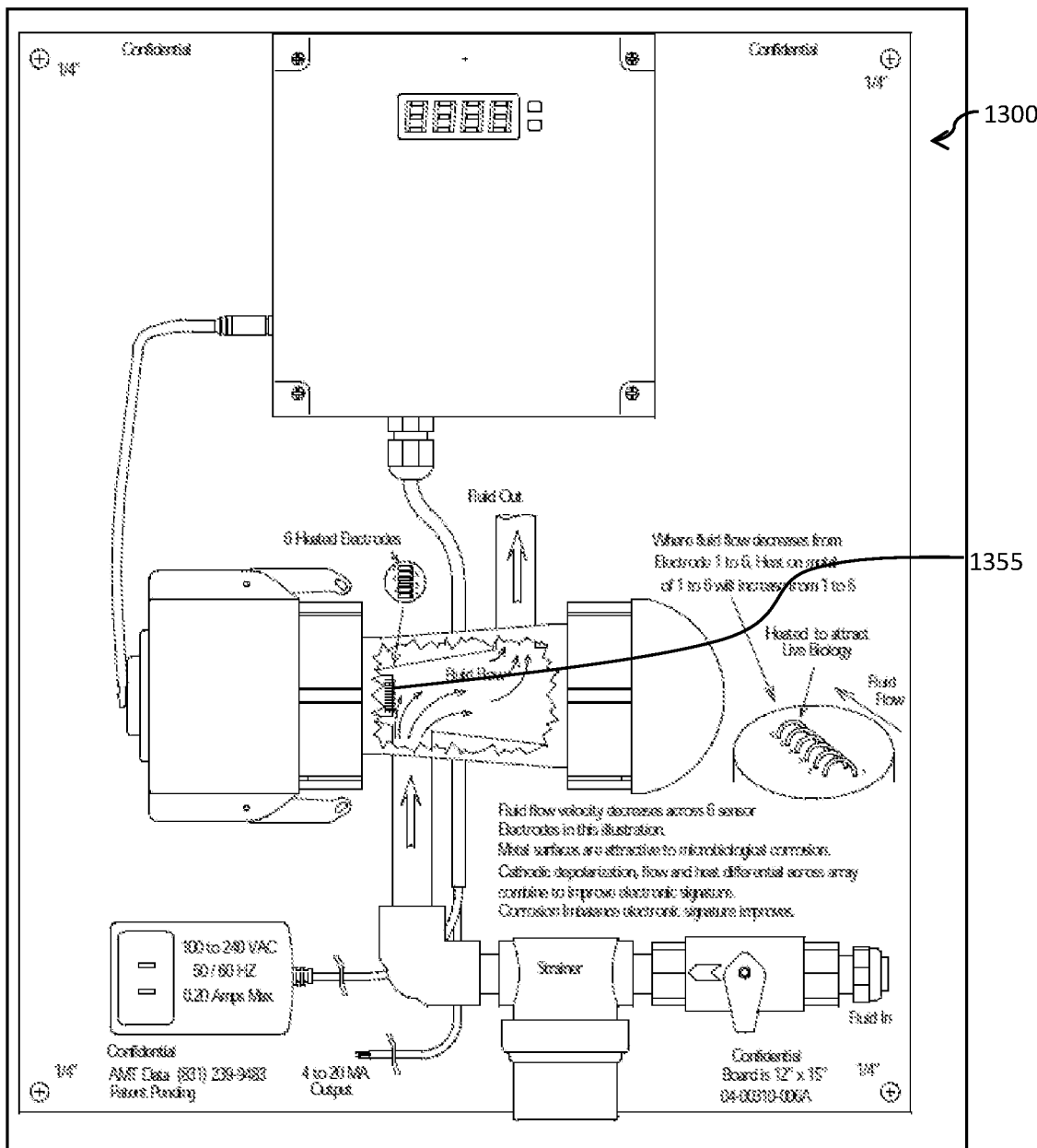
FIG. 15 is a system for bacteria detection using film formation promotion according to some embodiments of the present invention.

A series of test probes 1255 may include 6 sensor electrodes with metal surfaces attractive to microbial corrosion. The fluid velocity decreases along a vertical axis across array of sensors due to fluid dynamics within the sample flow chamber. The differential flow creates different micro-environments which may promote differential microbial growth on the different metal sensors. Using current readings as different voltage differentials are applied to the sensors, and with the use of switching polarity of the differential, as describe herein, allows for detection of live mircro-organisms on a much quicker time scale than with conventional methods. In some embodiments, as seen in FIG. 15, a test system 1300 is similar to that of FIG. 14 with the sensor array 1355 made up of protruding metal electrode rings.

Figures 16A, 16B:
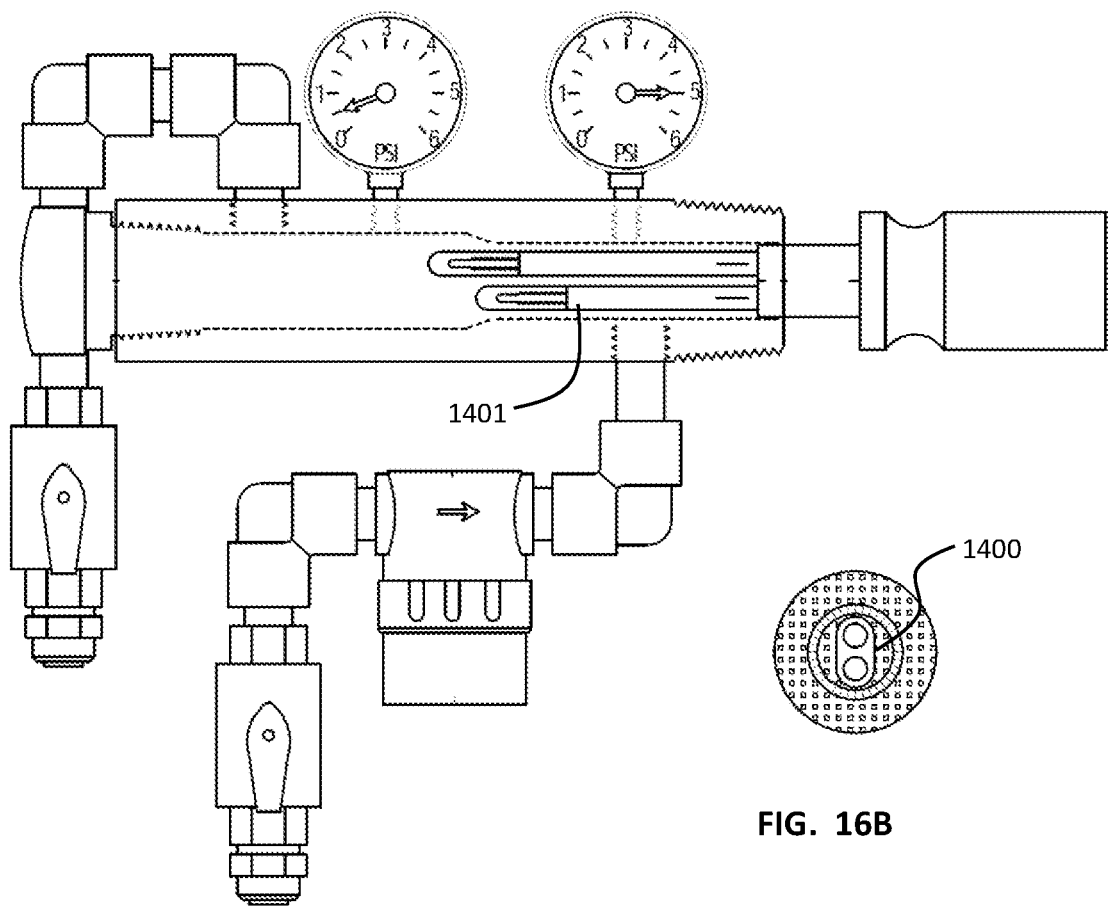
FIG. 16A is a system for bacteria detection using film formation promotion with a flow restriction device according to some embodiments of the present invention.
FIG. 16B is a flow restriction device according to some embodiments of the present invention.
Figure 17:
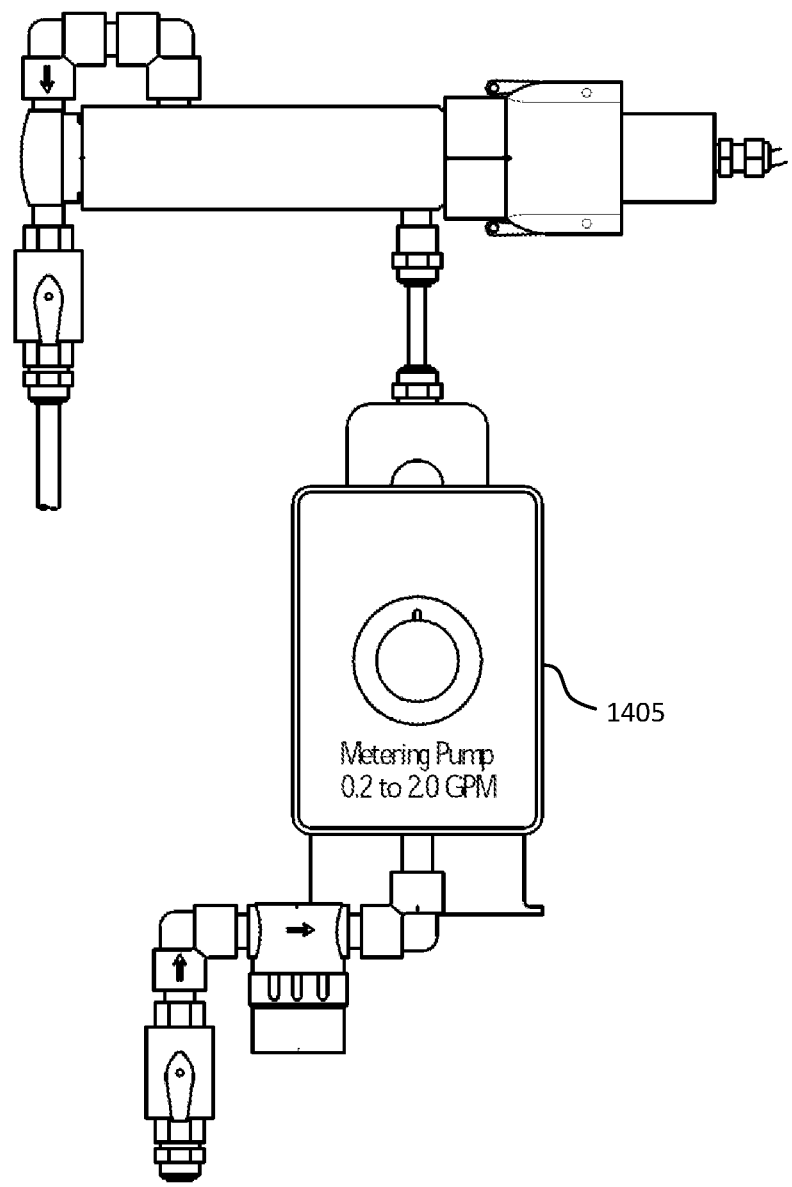
FIG. 17 is a system for bacteria detection using film formation promotion according to some embodiments of the present invention.

In some embodiments, as seen in FIGS. 16A and 16B, a flow restriction orifice 1400 may be used within the narrow entry section 1401 of the sample flow chamber. The use of the flow restriction orifice may allow an operator to tune the absolute and/or relative flow rate of the flowing liquid as they pass the first sensor tip and the second sensor tip. The use of a flow restriction orifice may bring the flow rate down and also accentuate the difference in flow rate between the two sensor tips.

An exemplary embodiment may be calibrated to operate with fluid flow velocities between 0.5 feet per second and 10.0 feet per second in the small id section of the sample chamber. Over this range, the larger id section will have 25 times less fluid flow velocity over a portion of the sensor element most extended into the larger id portion of the sample chamber. Under some applications, the fluid flow may be started and stopped at time intervals between 1 to 23 hours on, in each 24 hour period. The fluid flow velocity may be as high as 20 feet per second in the smaller id section of the sample chamber. In some aspects, not all of a sensor tip be in one constant velocity of fluid flow, similarly 100 percent of the other sensor tip may not be in another and different constant velocity of fluid flow. Part of the sensor tips may have a variable fluid flow velocity over each. In such a circumstance the average fluid flow velocity over all of one sensor tip will still be different than the average fluid flow velocity over all of the second sensor tip.

A exemplary ratio of cross-sectional areas for flow in the sample chamber is: Flow Outlet side: 0.736310778 sq-in. to flow Inlet side: 0.029351832 sq-in., the ratio of which is: 25 to 1. In some aspects, the ratio will be in a range of 1.5:1 to 50:1. In some aspects, a significant dynamic pressure drop may not take place until the ratio is more than 20 to 1.

In a measurement method according to embodiments of the present invention, fluid flows into the sample flow chamber via an inlet. In some embodiments this fluid is water diverted from a water system. The fluid flows through the sample flow chamber and exits via an outlet. Within the sample flow chamber are two test probes subjected to different environments. In some aspects, the two test probes may have different flow rates around their tips which has been induced by varying the cross-sectional flow area through the sample flow chamber. In some aspects, the two test probes are at different temperatures. In some aspects, both the flow rate and temperature differ between the two test probe tips.

The two test tips are subjected to a voltage differential and the current between the two test probe tips is monitored and recorded. The polarity of the voltage is then reversed and the current is also then monitored and recorded. In some aspects, each polarity is maintained for the same amount of time between reversals. In some aspects the time is 3 minutes. In some aspects the time between reversals is in the range of 1-5 minutes. A change in current over time is expected even in the absence of live microbes due to general corrosion.

The different environments on the two test probe tips result in different colonization types. The difference will be enough to result in a net electron flow between the two tips due just to the different types of corrosion going on at the two test probe tips. This net current will rise to a level that can be seen in the current measurements taken across the two tips. As the induced current due to the applied voltage reverses every few minutes, in one polarity direction the differential corrosion current will add to the induced current, and in the other polarity direction the differential corrosion current will subtract from the induced current. This difference in the absolute value of the current indicates that film forming bacteria have begun to corrode the tips. This in turn indicates that there are indeed live film forming bacteria in the tested liquid sample.

The use of differing environments on the two test tips allows for measurement of microbe influenced corrosion, thus detecting live film forming bacteria much more quickly than prior methods. For example, detection can occur on the order of 4 hours after the live bacteria have infiltrated the system. In other aspects, detection may occur on the order of 12 hours. The detection can occur before the main system has filmed up to the point of significant impact to the water system, allowing for possible treatment of the water with a biocide before significant impact to the water system.

A description of the data displayed and the data provided as 4 to 20 MA output for interface to monitoring systems may be as described below. To provide a useful output in response to the electrical signatures present on the sensor elements, changes in the electrical signature may be measured, displayed, and provided as an output to monitoring equipment in a variety of ways.

In some applications, the lowest readings may not necessarily represent the presence of live mixed species bacteria, archaea and/or fungi. The presence of direct current stray current in electrically conductive fluid may be detected by any sensor elements in any conductive fluid being monitored. Therefore, in applications where continuous monitoring will be established, a base line may be studied to account for the lowest readings observed. If the baseline is found to be an issue of concern, an investigation may be called for. Stray current of the direct current variety may continuously or intermittently affect many sensors in electrically conductive fluids. ORP sensors, for example, are often affected by stray current.

A suitable method to remove stray current from sensitive electrical sensor elements is to incorporate two sections of stainless steel pipes several feet upstream and downstream of the fluid conduit where monitoring is taking place. By grounding the 2 sections of stainless steel pipes, any stray current in the fluid will be removed from the fluid.

When mixed species biofilms become established on sensor elements, they begin to support charge transfers of electrical energy through their metabolic processes, such as: Sulfate reduction; Sulfur oxidation; Iron or manganese oxidation; Iron reduction; Organic acid production; and Cathodic depolarization through hydrogen utilization.

In stable fluids without stray current or live biology, very little difference in potential between the like metal sensor elements in the fluid is expected. If we observe rapid and sudden changes in the data, this may indicate the presence of stray current from ungrounded equipment in electrical association with the conductive fluid we are monitoring.

As biology begins to support charge transfer, the net electrical energy difference is usually a significant increase in the data displayed and monitored. In methods according to embodiments of the present invention, the polarity of the charge transfer is encouraged and is not left to random chance. The polarity of any stray dc current in the conductive fluid may add or subtract from the reading. A rapid and sudden shift in the data up or down may be an indication of stray current. After the influence of stray current is eliminated, an increase over the course of a day or more is a measurement of the net charge transfer.

From controlled testing with water drawn from ground wells, streams and ponds, as the data on the display nears or exceeds a reading of 5.0 units of measure, biofilm will always be found on the sensor elements.

When live biology first attach to the sensor elements there is no detectable charge transfer from the first attachments. Over the course of a number of hours or a few days, as the live biology colonize the sensor surfaces the charge transfer begins to be recognizable. In very active biology there is usually an increasing rate of detectable charge transfer within days. After quite some time, such as several weeks or months the detectable electrical signature decreases and becomes masked by the mature biofilm.

The detectable charge transfer increase more rapidly in response to the growth and maturity of the recently established biofilm. This often represents a non-linear increase in the reading on the display. Where the data ramps more rapidly after being low and somewhat flat, there is an indication that a biofilm is more strongly influencing the charge transfer between the two sensor elements.

If the sensor elements are not replaced after a biofilm event and left in place for months, the electrical signature will decrease over time and may become useless. Continuous monitoring of the data and a review of the entire data from the time the sensor elements were newly installed is recommended. Setting an alarm to detect an increase above baseline will also alert users to carefully inspect the fluid conditions and/or sensor elements.

In some aspects, the control electronics 168 may include an alarm, which may be set to alarm at a level of current imbalance above a certain level. The control electronics reading may be an interpretation of the current imbalance and may read out a different unit, which may be termed a biofilm unit.

As evident from the above description, a wide variety of embodiments may be configured from the description given herein and additional advantages and modifications will readily occur to those skilled in the art. The invention in its broader aspects is, therefore, not limited to the specific details and illustrative examples shown and described. Accordingly, departures from such details may be made without departing from the spirit or scope of the applicant's general invention.

What is claimed is:

1. A method for the detection of live film forming microbes in liquid by stimulating differential growth, said method comprising the steps of:
   routing a liquid through an inlet of a sample flow chamber;
   flowing a liquid through said sample flow chamber, said sample flow chamber comprising a first test probe and a second test probe, said liquid flowing first past said first test probe and then past said second probe;
   placing a voltage differential of a first magnitude and a first polarity across said first test probe and said second test probe as a first voltage state;
   measuring an electric current flow between said first test probe and said second test probe in said first voltage state;
   placing a voltage differential of the first magnitude and a reversed polarity of said first polarity across said first test probe and said second test probe as a second voltage state;
   measuring the electric current flow between said first test probe and said second test probe in said second voltage state; and
   contrasting the electric current flow in said first voltage state and said second voltage state to detect the presence of microbially influenced corrosion,
   wherein a fluid flow velocity around said first test probe is greater than the fluid flow velocity around said second test probe, thereby creating a first test environment with a first fluid flow velocity at said first test probe and a second test environment with a second fluid flow velocity at said second test probe.

2. The method of claim 1 wherein the ratio of the fluid flow velocity around said first test probe to the fluid flow velocity around said second test probe is in the range of 1.5:1 to 50:1.

3. The method of claim 1 wherein the ratio of the fluid flow velocity around said first test probe to the fluid flow velocity around said second test probe is greater than 20:1.

4. The method of claim 1 wherein said second test probe comprises a heater embedded within said second test probe, and wherein said second test probe is heated at least 20 degrees warmer than said first test probe.

5. A method for the detection of live film forming microbes in liquid by stimulating differential growth, said method comprising the steps of:
   routing a liquid through an inlet of a sample flow chamber;
   flowing a liquid through said sample flow chamber, said sample flow chamber comprising a first test probe and a second test probe, said liquid flowing first past said first test probe and then past said second probe;
   placing a voltage differential of a first magnitude and a first polarity across said first test probe and said second test probe as a first voltage state;
   measuring an electric current flow between said first test probe and said second test probe in said first voltage state;
   placing a voltage differential of the first magnitude and a reversed polarity of said first polarity across said first test probe and said second test probe as a second voltage state;
   measuring the electric current flow between said first test probe and said second test probe in said second voltage state; and
   contrasting the electric current flow in said first voltage state and said second voltage state to detect the presence of microbially influenced corrosion,
   wherein said sample flow chamber further comprises a heater adapted to heat the fluid after it has passed said first test probe and before it has passed said second test probe, wherein the heater is located in between the first test probe and the second test probe, thereby creating a first test environment of a first temperature at said first test probe and a second test environment of a second temperature at said second test probe.

6. The method of claim 5 wherein the fluid around said second test probe is in the range of 10 degrees C. to 60 degrees warmer than the fluid around said first test probe.

7. The method of claim 5 wherein said second test probe is heated by the heated fluid in the range of 10 degrees C. to 60 degrees warmer than said first test probe.

8. The method of claim 5 wherein said second test probe is heated by the heated fluid at least 20 degrees warmer than said first test probe.

9. A method for the detection of live film forming microbes in liquid by stimulating differential growth, said method comprising the steps of:
   routing a liquid through an inlet of a sample flow chamber;
   flowing a liquid through said sample flow chamber, said sample flow chamber comprising a first test probe and a second test probe, said liquid flowing first past said first test probe and then past said second probe;
   placing a voltage differential of a first magnitude and a first polarity across said first test probe and said second test probe as a first voltage state;

measuring an electric current flow between said first test probe and said second test probe in said first voltage state;

placing a voltage differential of the first magnitude and a reversed polarity of said first polarity across said first test probe and said second test probe as a second voltage state;

measuring the electric current flow between said first test probe and said second test probe in said second voltage state; and contrasting the electric current flow in said first voltage state and said second voltage state to detect the presence of microbially influenced corrosion, wherein said second test probe comprises a heater embedded within the second test probe, wherein said second test probe is heated in the range of 10 degrees C. to 60 degrees warmer than said first test probe, thereby creating a first test environment of a first temperature at said first test probe and a second test environment of a second temperature at said second test probe.

10. The method of claim 9 wherein said second test probe is heated at least 20 degrees warmer than said first test probe.

\* \* \* \* \*